United States Patent
Pogge Von Strandmann

(10) Patent No.: US 6,750,198 B1
(45) Date of Patent: Jun. 15, 2004

(54) PREPARATION FOR THE TREATMENT OF PIGMENTATION DISORDERS

(75) Inventor: Elke Pogge Von Strandmann, Bochum (DE)

(73) Assignee: Fumedica GmbH, Herne (DE)

( * ) Notice: Subject to any disclaimer, the term of this patent is extended or adjusted under 35 U.S.C. 154(b) by 0 days.

(21) Appl. No.: 10/019,708

(22) PCT Filed: Feb. 22, 2000

(86) PCT No.: PCT/EP00/01822

§ 371 (c)(1),
(2), (4) Date: Dec. 27, 2001

(87) PCT Pub. No.: WO00/50070

PCT Pub. Date: Aug. 31, 2000

(30) Foreign Application Priority Data

Feb. 25, 1999 (DE) .......................... 199 08 242
Jul. 27, 1999 (DE) .......................... 199 34 458

(51) Int. Cl.[7] .............................. A61K 38/16
(52) U.S. Cl. ............................ 514/2; 514/21
(58) Field of Search ........................ 514/2, 21

(56) References Cited

U.S. PATENT DOCUMENTS

| | | |
|---|---|---|
| 5,403,712 A | 4/1995 | Crabtree et al. |
| 5,620,887 A | 4/1997 | Crabtree et al. |

FOREIGN PATENT DOCUMENTS

| | | |
|---|---|---|
| WO | 91/16024 | 10/1991 |

OTHER PUBLICATIONS

Schallreuter, Karin U. et al. (1994) "Defective tetrahydrobiopterin and catecholamine biosynthesis in the depigmentation disorder vitiligo", Biochimica et Biophysica Acta, vol. 1226, No. 2, pp. 181–192.

Strandmann, Elke Pogge V. et al. (1998) "The bifunctional protein DcoH/PCD, a transcription factor with a cytoplasmic enzymatic activity, is a maternal factor in the rat egg and expressed tissue specifcally during embryogenesis", International Journal of Developmental Biology, vol. 42, No. 1, pp. 53–59.

Li, Lingna et al. (1997) "Topical liposome delivery of molecules to hair follicles in mice", Journal of Dermatological Science, vol. 14, No. 2, pp. 101–108.

V. Strandmann Elke Pogge et al. (2000) "Ectopic pigmentation in Xenopus in response to DcoH/PCD, the cofactor of HNF1 transcription factor/pterin–4alpha–carbinolamine dehydratase", Mechanisms of Development, vol. 91, No. 1–2, pp. 53–60.

D. B. Mendel et al, (1991), Science 254, p. 1762. (to follow).

B.A. Citron et al. (1992), Proc. Natl. Acad. Sci. USA 89, p. 11891. (to follow).

E. Pogge V. Strandmann and G.U. Ryffel (1995), Development 121, p. 1217. (to follow).

E. Pogge V. Strandmann et al. (1998), Int. J. Dev. Biol. 42, p. 53. (to follow).

D. B. Mendel et al. (1991), Science 254, p. 1762. (to follow).

R.M. Hoffman (1997), Jornal of Drug Targeting, vol. 6, p. 67. (to follow).

E. Pogge Von Strandmann and G.U.Ryffel (1995), Development 121, pp. 1217–1226. (to follow).

*Primary Examiner*—Jean C. Witz
(74) *Attorney, Agent, or Firm*—Collard & Roe, P.C.

(57) ABSTRACT

The invention relates to a preparation for the treatment of pigmentation disorders. The preparation contains a physiologically active quantity of the DCoH protein, the DNA and/or RNA coding for the protein or DCoH antibodies or antiserum as active ingredient in a pharmaceutically suitable excipient. The invention also relates to the use of DCoH, the DNA and/or RNA coding for same or DCoH antibodies or antiserum as active ingredient in the production of such a preparation.

1 Claim, 3 Drawing Sheets

PREPARATION FOR THE TREATMENT OF PIGMENTATION DISORDERS

CROSS REFERENCE TO RELATED APPLICATIONS

Figure 1:
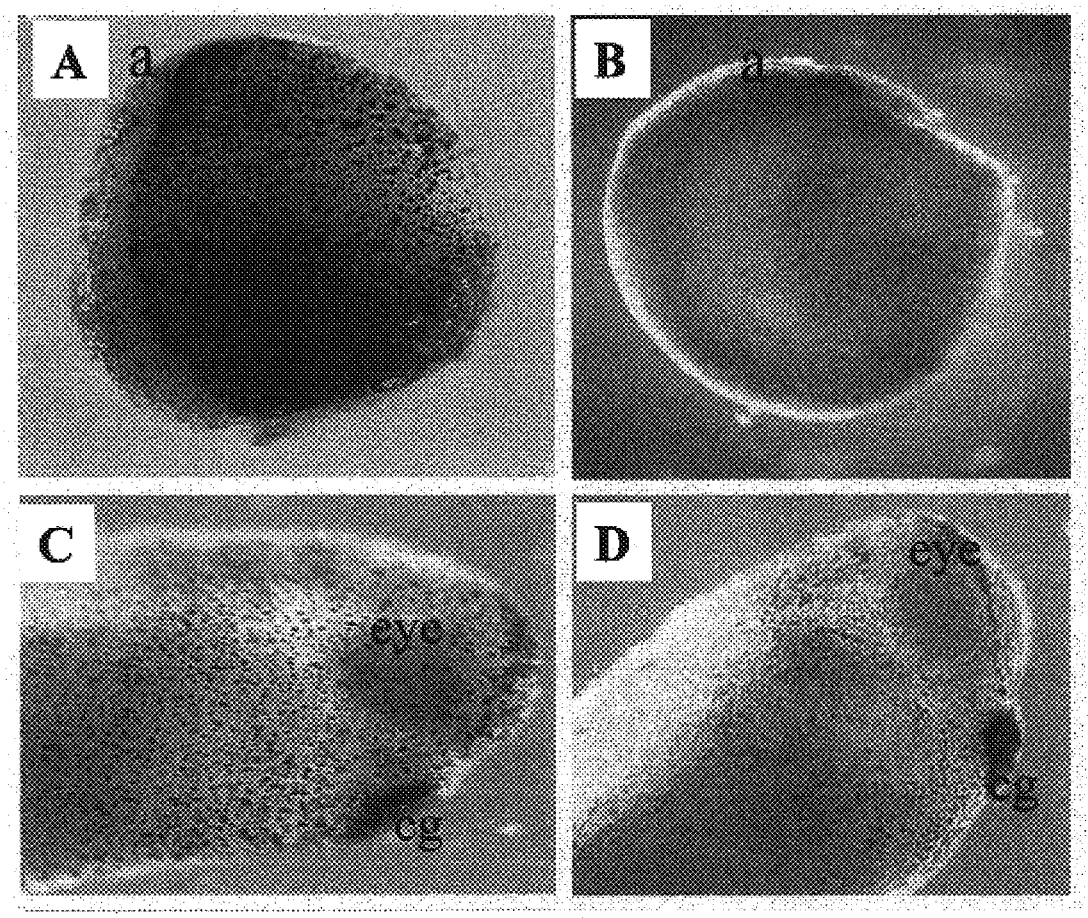

Applicant claims priority under 35 U.S.C. §119 of German Application Nos. 199 08 242.1 and 199 34 458.2 filed Feb. 25, 1999 and Jul. 27, 1999, respectively. Applicant also claims priority under 35 U.S.C. §120 of PCT/EP00/01822 filed Feb. 22, 2000. The international application under PCT article 21(2) was not published in English.

The invention relates to a preparation for the treatment of pigmentation disorders of the human and animal body with the use of the protein DCoH and the DNA and/or RNA coding for said protein as the active ingredient.

The enzyme DCoH of the dimerization factor of the HNF-1 homeodomanial proteins (HNF-1∝ and HNF-1β). DCoH is participating by means of said mechanisms in the control of the gene expression (see D. B. MENDEL ET AL in Science 254 (1991; page 1762). The protein is known at the same time as the ptrin-4∝-carbinolamine-dehydratase PCD and participates in the tetrahydrobiopterin regeneration (see B. A. CITRON ET AL, Proc. Natl. Acad. Sci. USA 89; 1992; page 11891). PCD engages in the process of the biosynthesis of L-tyrosine from L-phenylalanine. In the latter cycle, PCD is tied in together with phenyl-alanine hydroxylase and participates in the regeneration of (6R)5, 6,7,8-tetrahydrobiopterin. Independently thereof, however, DCoH/PCD is found also in the vertebral El. and in the pigmented epithelium of the eye, and in the skin and the brain—see E. POGGE V. STRANDMANN and G. U. RYFFEL, Development 121 (1995); page 1217; E. POGGE V. STRANDMANN ET AL in Int. J. Dev. Biol. 42 (1998) page 53).

After the first data on the purification and cloning of DCoH were supplied by D. B. MENDEL ET AL in Science 254 (1991), page 1762, both the peptide sequence and the nucleic acid sequence of human, mouse and rat-DCoH coding for said protein have been described for the first time in U.S. Pat. Nos. 5,403,712 and 5,620,887. Reference is made to said patents with respect to all relevant structural data. DCoH/PCD has been found to be a more or less universal principle in the development of vertebrae, in particular also for their early development. It possesses both catalytic as well as regulating properties and is present in a greater number of types of cells. It is closely associated in some of said cell types with the nuclear transcription factors HNF-1∝ and HNF-1β, and in other cell types it is tied into the phenylalanine-hydroxylase enzyme complex. The presence of DCoH/PCD in cell types in the absence of HNF-1or phenylalanine-hydroxylase suggests that the protein also cooperates with cellular partners that are different from those cell types.

Vitiligo, for example, is a known pigmentation disorder. Vitiligo is characterized by white, pigment-free, mostly gradually growing patches with a hyperpigmented edge and is attributed to an inhibition of the melanin synthesis. The phenomenon may occur in conjunction with other diseases such as diabetes mellitus. No causal treatment has been possible until now. Vitiligo seems to be associated with an insufficiency of DCoH.

Other pigmentation disorders are, for example forms of canities, i.e. grayness of the hair, both in the physiological form occurring prematurely and at higher age levels. In this instance, too, no causal therapies are known.

A disease that is linked with phenomena of de-pigmentation is alopecia areata, which is a local, suddenly beginning and causally unclear loss of hair, in particular also of the hair of the head. In connection with this type of loss of hair, the hair follicles are preserved, but remissions occur spontaneously in the course of which the affected hair is (first) growing again white. The disease is therefore connected with a pigmentation disorder.

Furthermore, the Usher syndrome and the Waardenburg syndrome are connected with pigmentation disorders. Moreover, numerous disorders are known that are connected with (local) hyperpigmentation.

The effects of the phenomena and diseases mentioned above have been described in great detail; however, it has not been possible to clarify their causes. The assumption that the peptide DCoH/PCD might play a role in this connection has been expressed with respect to vitiligo; however, this has not been proven. Many factors do in fact suggest that the reduction of the enzymatic activity of DCoH observed in connection with mild forms of hyperphenylalaninemia and vitiligo may be a consequence but not the cause of said disorders. It has been proven that an excess supply of the cofactor tetrahydrobioterine required for the formation of L-tyrosine from L-phenylalanine is present in the affected cells.

Overall, there is a need for preparations that are suited for the treatment of pigmentation disorders of the human and animal body and of the phenomena connected with such disorders.

It has now been surprisingly found that DCoH/PCD is suitable for creating de novo pigmented cells. In this process, DCoH is not a link in the melanin synthesis whose absence leads to de-pigmentation, but an "artificial hyper-expression" takes place that triggers the pigmentation. Furthermore, it has been found that DCoH antiserum is suited for weakening pigmentation or for preventing it (its occurrence).

Therefore, the object of the invention is a preparation for the treatment of pigmentation disorders in which a physiologically active amount of the protein DCoH, of the DNA and/or RNA coding for said protein, or of DCoH-antibodies is contained as the active ingredient in a pharmaceutically acceptable excipient.

The preparation as defined by the invention contains the protein DCoH triggering the pigmentation, or as an alternative or supplement the DNA and/or RNA coding for said protein, or as an alternative DCoH-antibodies or antiserum as the active ingredients.

The effect of DCoH/PCD has been demonstrated experimentally after mRNA was injected into oocytene. Since the RNA in the cell is the product of the transcription of the corresponding DNA, and is itself transformed into the protein, the efficiency of all three active ingredients, i.e. of the protein, the DNA and the RNA, is secured, whereby certain spectra may occur with respect to the intensity and duration of the effect. The protein sequence and the nucleic acid sequence of DCoH and of the DNA coding for said protein are described in U.S. Pat. Nos. 5,403,712 and 5,620,887. The preparation of antiserum has been described in Development 121, page 1217 (1995). In detail, both poly- and monoclonal antibodies can be considered for the purpose as defined by the invention.

The preparation as defined by the invention for the treatment of pigmentation disorders contains the active ingredient in a usually employed, pharmaceutically acceptable and compatible excipient. Such excipients are known both for topical and parenteral administration. Possible are, furthermore, gene-therapeutic forms of administration in connection with which the gene decoding for the DCoH is introduced into the target cell. The concentrations of the active ingredient are the same as commonly applied in the field of protein/DNA/RNA therapy and are oriented on the concentrations normally found in the target cells, i.e. such concentrations are at the normal level or higher.

In topical administrations, the preparation can be applied to the skin, whereby the active ingredient is contained in a transdermally effective excipient. Such excipients, which are conceived in the present case in the form of penetration aids or penetration accelerators and present in most cases in the form of liposomes, are known. Furthermore, the preparation may be applied by means of a transdermal system, which is useful particularly in the treatment of local disorders.

In topical applications that are directed at certain regions or cells, for example in connection with hyper-pigmented or de-pigmented regions of the skin or areas of hair growth, especially the application of liposomes developed for that purpose is recommended, such as the liposomes described by R. M. HOFFMAN in the Journal of Drug Targeting, vol. 6 (1997), 67. HOFFMANN describes the hair follicle-selective introduction of macromolecules up to the active gene with a target system based on topically applied liposomes based on phosphatyl choline. The system is applicable to melalins, proteins, genes and the like introduced into liposomes or bonded to the latter.

Cationic lipids for the intracellular dispensing of biologically active molecules are known, furthermore, from WO-A 91/16024, whereby such cationic lipids can be employed for the topical, enteral and also parenteral administration of active ingredients.

It may be useful in many cases to make the active ingredient available systemically in a manner as it is known, for example from the interferon-therapy of multiple sclerosis or also in the treatment of diabetes. Said therapies are based on the uniform distribution of the active ingredient in the body and the effect triggered by such uniform distribution. The active ingredient can be used in this connection as such or also in a modified form, i.e. in forms that release the actual active ingredient only in the target site. Suspensions for parenteral administration usefully contain the active ingredient also bonded to or included in liposomes acting as the transfer medium, and suspended in a physiologically acceptable carrier liquid.

Another systemic form of administration, for example, is in the form of a nasal spray that transports the active ingredient onto the mucous membranes and delivers it to the body via such mucous membranes.

Another administration possibility is the implantation of pro- or eucaryotic organisms or of excipients containing the active ingredient. Such excipients secrete the active ingredient at a continuous or regulated rate.

Finally, reference is made to the possibilities offered by the gene therapy, i.e. the embedding of the gene for DCoH/PCD in a target cell by means of DNA- or RNA-viruses, which integrate into the genome and in this way introduce the gene in a stable manner. The gene is then subject to the normal transcription and translation into the cell and thus represents a useful alternative to transient transfection with the protein, or the DNA or RNA coding for said protein. The viruses may embed themselves in this connection locally (see also the p53-deficiency of melanomas), or may spread through the body in an undirected manner. Adenoviruses or other "cold viruses" that are modified for said purpose are described in the prior art and may be considered as suitable vehicles. Antisense techniques may be employed for excluding hyper-pigmentation.

It is understood that the protein or the DNA and/or RNA coding for said protein may be stabilized for storage purposes and for the purpose of avoiding any premature deterioration of the effect. Stabilization can be accomplished by adding the usual additives such as, for example buffer substances, salts of other proteins, as well as also salts of DNA and RNA. For example albumin, herring sperms, DNA and tRNA are known for said purpose from the field of molecular biochemistry, and also by adding detergents (thesiteR, tritonR), alkali and alkaline earth ions and the like. Storing the preparation and/or active ingredient in the dried or freeze-dried form, or after flash-freezing in liquid nitrogen may be useful as well.

The preparation as defined by the invention may, of course, contain the active ingredient in the modified form as well, i.e. in the form of protein in which individual amino acids are exchanged or missing. Likewise, nucleotides or nucleotide sequences may be missing, supplemented or exchanged in the DNA and/or the RNA. The precondition is that the active ingredient so modified will continue to still deliver the effect it is expected to supply in the treatment of de-pigmentation phenomena. Reasons for such modifications may be the stabilization of the active ingredient, production technology-related or formulation-technical grounds, or also an enhancement of the effect or spectrum of effects. Considered may be mutation and fusion according to gene-technological or chemical methods, as well as fusion with N- and C-terminal proteins or peptides. For reasons of superior purification by means of affinity chromatography, it is possible also to carry out, for example histidine tags or Gst fusions, or to insert sequences in order to facilitate the direction into defined target cells. NLS-sequences are suitable for directing the active ingredient into the core of the cell. By means of phosphorylation or glycolization on suitable radicals, and with the help of modifications on the phosphate group of the DNA or RNA it is possible also to effect modifications that prevent the degradation by the body's own nucleases. Phosphorus-thioate groups are known for said purpose.

For stabilizing the protein it may be useful to introduce changes, for example already at the level of the DNA/RNA, for example in order to eliminate sites of restriction, chemical instability, or points of attack of nucleases, or to intensity or specify the effect, for example also in order to discriminate between the various activities of the multifunctional protein, as well as for the purpose of deactivating an interfering function. Vice versa, it may be useful to reduce the stability and to thus reduce the half-time value of the active ingredient by introducing modifications that permit protolytic degradation, for example by incorporating recognition sequences for detecting proteases.

The protein can be isolated in the usual manner following cloning of the gene in suitable vectors recombined from bacteria or eucaryonts. The DNA and the RNA can be obtained from bacteria or eucaryonts according to standard methods.

The preparation as defined by the invention for the treatment of pigmentation disorders contains the active ingredient in a pharmaceutically acceptable excipient that may be comprised of several of the usual components, on the one hand. The excipient in turn usefully contains a transfer medium suitable for the active ingredient, in particular a liposome or a virus. The preparation is primarily intended for topical or parenteral administration.

In addition to a preparation for treating pigmentation disorders, the invention also relates to the use of DCoH, the DNA and/or RNA coding for said protein, or DCoH antibodies or DCoH antiserum as the active ingredient for the preparation of a medication for treating pigmentation disorders of the human and the animal body. In particular, pigmentation disorders are understood to constitute de-pigmentation phenomena of the skin, hair and the retina, including in particular vitiligo, alopecia areata, as well as the premature or age-conditioned graying of the growth of hair, and also forms of local hyperpigmentation such as, for example melanoderma, nevus and the like. The invention relates to both congenital and acquired pigmentation disorders.

Another field of application of the DCoH as defined by the invention, the DNS and/or RNA coding for said protein, or DCoH antibodies or DCoH antiserum containing the preparation is the treatment of melanocytic tumors. Melanocytic tumors and in particular also the malignant melanoma represent de-differentiated melanocytes of clonal origin.

The preparation as defined by the invention is acting on melanocytic tumors in two directions. On the one hand, its effect is based on the re-differentiation of de-differentiated melanocytes. Tests on xenopus oocytes have shown that DCoH initiates the differentiation of melanocytes. The application of the preparation as defined by the invention thus acts in the direction of re-differentiation and normalization of degenerated cells.

On the other hand, it is possible to influence the division of the melanocytes via suitable mutants of the DCoH-DNA, DCoH-RNA or the protein itself. Via blocking of the effect of the DCoH it is possible to influence the rate of division of the melanocytes up to standstill of the division, and even up to killing the cells.

The invention is explained in greater detail in the following, whereby reference is supplementarily made to E. POGGE VON STRANDMANN and G. U. RYFFEL, Development 121 (1995), pages 1217 to 1226.

EXAMPLE 1

Frogs of the Xenopus species were maintained under standard conditions. For in vitro insemination, 600 U gonadotrophin (human) was subcutaneously injected into the dorsal lymph sac of sexually mature females; the eggs were placed in Petri dishes and then fertilized with intact sperms. After 5 minutes, top coating was carried out with 88 mM NaCl, 1 mM KCL, 0.7 mM CaCl , 1 mM MgSO, 5 mM Hepes ph 7.8, and 2.5 mM NaHCO.

For the micro-injection, the gel coat was removed and then treated for 1.5 minutes with 2% cysteine at ph 8.0, and subsequently washed three times in top coating buffer. Following the injection, cultivation was carried in overcoating buffer at room temperature.

mRNA obtained by in vitro transcription from suitable recombined vectors was used for the injection. 500 pg/RNA in 25 nl buffer solution was injected per egg. The small glass tubes used for said purpose were drawn from capillaries prior to their use and had a diameter of not more than 30 $\mu$m at the tip.

The embryos developed from the eggs exhibited a distinct pigmentation that started earlier than in the control stage. Furthermore, pigmentation occurred in sites where the embryo is normally not pigmented.

FIG. 1 shows embryos that over-express DCoH in the left row of the images (A/C). The control is located on the right row of images (B/D). The dark pigmentation patches are clearly visible in the left row of images. The abbreviations designate the following: a=anima; eye=eye; cg=cement glant.

DCoH/PCD thus induces ectopic pigment cells. The result shows that DCoH/PCD alone, i.e. without the melanin synthesis chain, is capable of triggering the steps required for the pigment synthesis.

EXAMPLE 2

In the present example, the RNA for the DCoH in xenopus embryos in the 2 cell stage is injected only into one of the two cells, together with the RNA's for the GFP=green fluorescent protein. The co-injection of the RNA for the GFP served the purpose of visualizing that the injected RNA's are also translated into active protein only in the injected cells.

Figure 2:
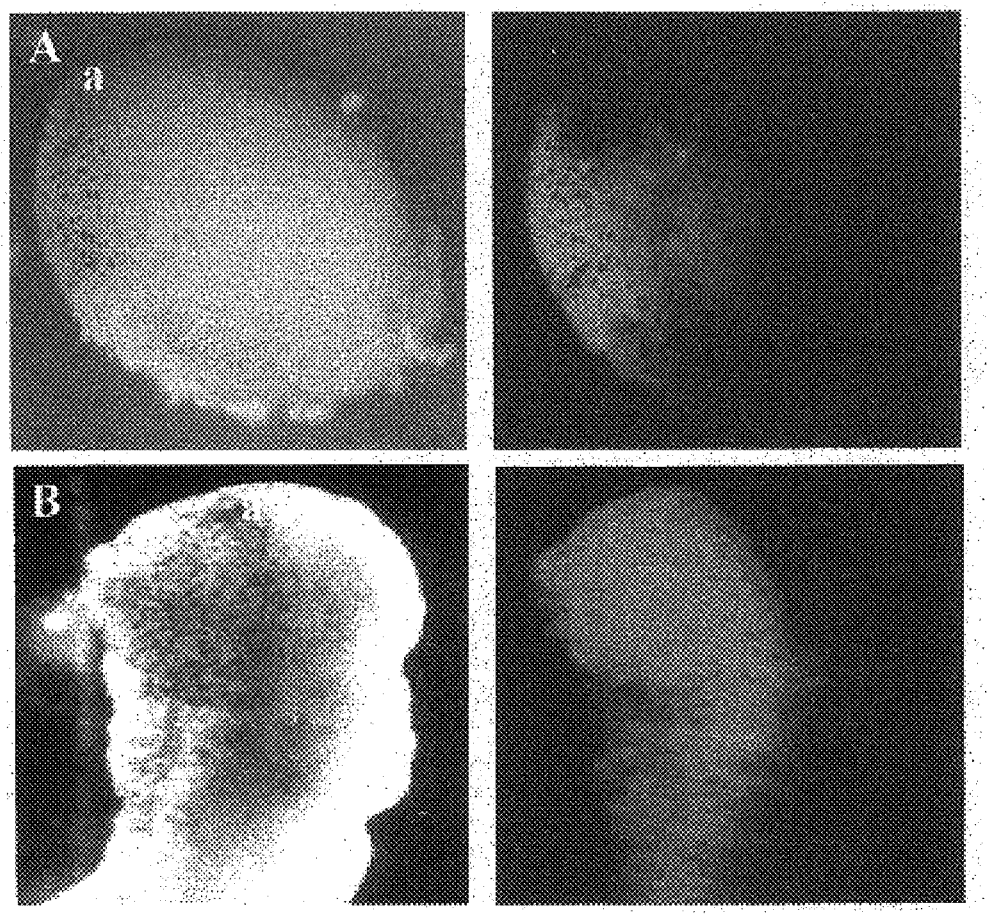

FIG. 2 shows that in the larvae developing from the second cell stage, the pigmentation is limited to one half of the body of the larvae, namely where the fluorescence is visible as well (right-hand row of images). DCoH/PCD is thus suited to trigger a premature pigmentation and pigmentation beyond the normal measure in the cells into which it was admitted. The larvae developed in a normal manner disregarding the hyperpigmentation and the fluorescence.

EXAMPLE 3

Figure 3:
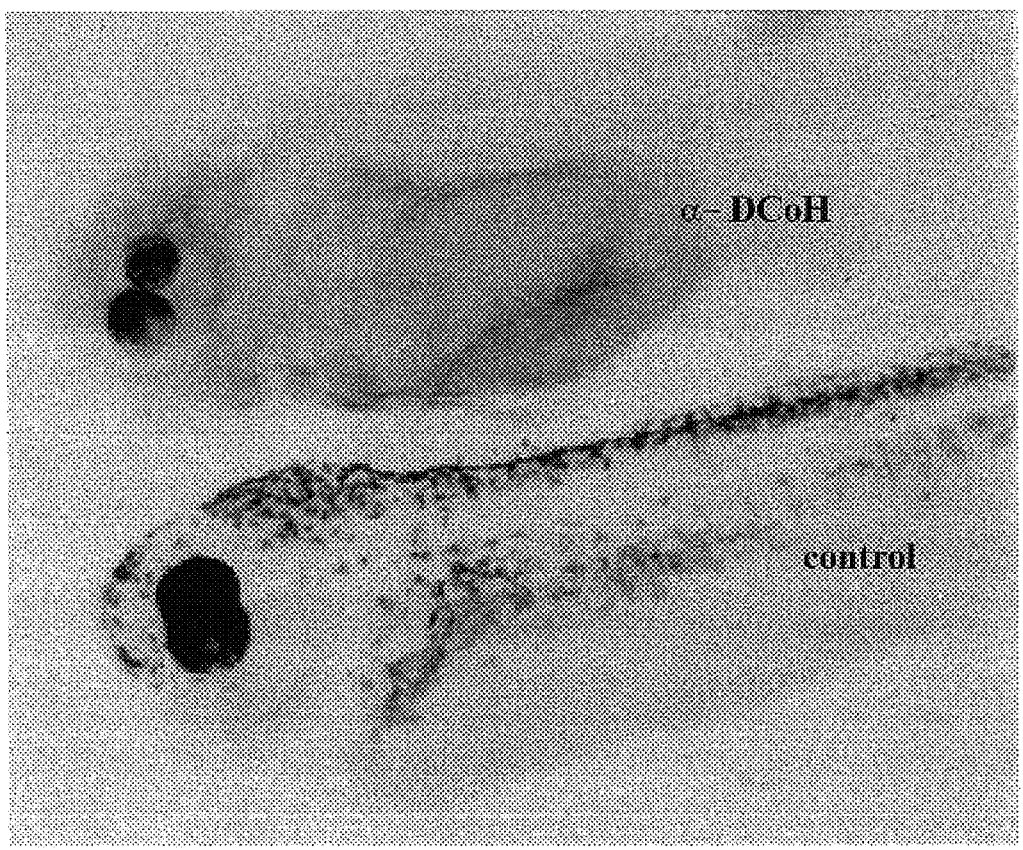

Antiserum against DCoH obtained according to standard methods in rabbits was injected analogous to example 2 into cells of frogs of the xenopus species. FIG. 3 shows that the formation of pigmentation is completely suppressed in embryos three days old ($\alpha$-DCoH, top image), whereas the normal pigmentation appears in the control (bottom image).

What is claimed is:

1. A method for treating disorders characterized by a reduction in pigmentation comprising administering an effective amount of the protein DCoH.

* * * * *